(12) United States Patent
Lin

(10) Patent No.: US 8,273,840 B2
(45) Date of Patent: *Sep. 25, 2012

(54) SILICONE POLYETHER ELASTOMER GELS

(75) Inventor: Shaow Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 714 days.

This patent is subject to a terminal disclaimer.

(21) Appl. No.: 12/293,580

(22) PCT Filed: Mar. 20, 2007

(86) PCT No.: PCT/US2007/006833
§ 371 (c)(1),
(2), (4) Date: Sep. 19, 2008

(87) PCT Pub. No.: WO2007/109240
PCT Pub. Date: Sep. 27, 2007

(65) Prior Publication Data
US 2010/0158824 A1 Jun. 24, 2010

Related U.S. Application Data

(60) Provisional application No. 60/784,340, filed on Mar. 21, 2006, provisional application No. 60/799,864, filed on May 12, 2006, provisional application No. 60/838,802, filed on Aug. 18, 2006.

(51) Int. Cl.
*C08G 77/08* (2006.01)

(52) U.S. Cl. ............ 528/15; 528/31; 524/268; 524/588; 424/401

(58) Field of Classification Search .................... 528/15, 528/31; 524/588, 268; 424/401
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,296,291 A | 1/1967 | Chalk |
| 3,419,593 A | 12/1968 | Willing |
| 3,516,946 A | 6/1970 | Modic |
| 3,814,730 A | 6/1974 | Karstedt |
| 3,928,629 A | 12/1975 | Chandra et al. |
| 3,989,668 A | 11/1976 | Lee et al. |
| 4,122,029 A | 10/1978 | Gee et al. |
| 4,987,169 A | 1/1991 | Kuwata et al. |
| 5,036,117 A | 7/1991 | Chung et al. |
| 5,175,325 A | 12/1992 | Brown et al. |
| 5,236,986 A | 8/1993 | Sakuta |
| 5,380,527 A * | 1/1995 | Legrow et al. ................ 424/401 |
| 5,387,417 A | 2/1995 | Rentsch |
| 5,412,004 A | 5/1995 | Tachibana et al. |
| 5,493,041 A | 2/1996 | Biggs et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,869,727 A * | 2/1999 | Crane et al. ................... 556/445 |
| 5,880,210 A | 3/1999 | Schulz, Jr. et al. |
| 5,889,108 A | 3/1999 | Zhang |
| 5,919,441 A | 7/1999 | Mendolia et al. |
| 5,929,162 A | 7/1999 | Horne et al. |
| 5,929,164 A | 7/1999 | Zhang |
| 5,981,680 A | 11/1999 | Petroff et al. |
| 5,998,542 A | 12/1999 | Horne et al. |
| 6,013,682 A | 1/2000 | Dalle et al. |
| 6,051,216 A | 4/2000 | Barr et al. |
| 6,200,581 B1 | 3/2001 | Lin et al. |
| 6,207,717 B1 | 3/2001 | Lin et al. |
| 6,262,170 B1 | 7/2001 | Kilgour et al. |
| 6,271,295 B1 | 8/2001 | Powell et al. |
| 6,291,563 B1 | 9/2001 | Horne et al. |
| 6,331,604 B1 | 12/2001 | Wang et al. |
| 6,365,670 B1 | 4/2002 | Fry |
| 6,528,584 B2 * | 3/2003 | Kennedy et al. .............. 525/101 |
| 6,531,540 B1 | 3/2003 | O'Brien |
| 6,605,734 B2 | 8/2003 | Roy et al. |
| 7,078,026 B2 | 7/2006 | Ferrari et al. |
| 7,211,108 B2 * | 5/2007 | Furst et al. ................... 623/1.44 |
| 8,016,881 B2 * | 9/2011 | Furst ........................... 623/1.46 |
| 2001/0041771 A1 | 11/2001 | Kondon et al. |
| 2003/0072730 A1 | 4/2003 | Tournilhac |
| 2003/0170188 A1 | 9/2003 | Ferrari et al. |
| 2003/0235553 A1 | 12/2003 | Lu et al. |

(Continued)

FOREIGN PATENT DOCUMENTS

| | | |
|---|---|---|
| EP | 0922734 | 6/1999 |
| EP | 1148099 | 10/2001 |
| EP | 1266648 | 12/2002 |
| EP | 1266653 | 12/2002 |
| EP | 1057872 | 2/2006 |
| EP | 1266647 | 5/2007 |
| JP | 06-049347 | 2/1994 |
| WO | WO99/13859 | 3/1999 |
| WO | WO01/14458 | 3/2001 |
| WO | 03/093349 | * 11/2003 |
| WO | WO03/093349 | 11/2003 |
| WO | WO03/093369 | 11/2003 |
| WO | WO 03093369 A1 * | 11/2003 |
| WO | WO03/101412 | 12/2003 |
| WO | WO03/105789 | 12/2003 |
| WO | WO03/105801 | 12/2003 |
| WO | WO03/106614 | 12/2003 |

(Continued)

OTHER PUBLICATIONS

"Synthesis of New Organic Crosslinking Reagents Containing SiH Bonds and Curing System Thereof" authored by Iwahara et al. and published in Polymer Journal (1993) 25 (4), 379-389.

*Primary Examiner* — Margaret Moore
(74) *Attorney, Agent, or Firm* — Alan Zombeck

(57) ABSTRACT

Gel compositions are disclosed containing a silicone polyether elastomer from the reaction of an organohydrogensiloxane having at least two SiH containing cyclosiloxane rings in its molecule, a compound or mixture of compounds having at least two aliphatic unsaturated groups in its molecule, and a hydrosilylation catalyst. The silicone polyether elastomer reaction product may itself be a gelled composition, or optionally may be contained in a carrier fluid to form a gel. The gel compositions may further contain a personal or healthcare active.

8 Claims, No Drawings

U.S. PATENT DOCUMENTS

| | | | |
|---|---|---|---|
| 2004/0091440 A1* | 5/2004 | Kamei et al. | 424/70.12 |
| 2004/0092655 A1 | 5/2004 | Otomo | |
| 2004/0180032 A1 | 9/2004 | Manelski et al. | |
| 2004/0228821 A1 | 11/2004 | Sunkel et al. | |
| 2009/0317343 A1* | 12/2009 | Lin et al. | 424/59 |
| 2010/0172849 A1* | 7/2010 | Shaow et al. | 424/59 |
| 2010/0183525 A1* | 7/2010 | Lin | 424/59 |

FOREIGN PATENT DOCUMENTS

| | | |
|---|---|---|
| WO | WO04/000247 | 12/2003 |
| WO | WO2004/054523 | 7/2004 |
| WO | WO2004/054524 | 7/2004 |
| WO | WO2004/060101 | 7/2004 |
| WO | WO2004/060271 | 7/2004 |
| WO | WO2004/060276 | 7/2004 |
| WO | 2004084844 | 10/2004 |
| WO | WO2004/103323 | 12/2004 |
| WO | 2005100444 | 10/2005 |
| WO | WO2007/109240 | 9/2007 |
| WO | WO2007/109260 | 9/2007 |
| WO | WO2007/109282 | 9/2007 |
| WO | WO2008/085360 | 7/2008 |
| WO | 2009042535 | 4/2009 |

* cited by examiner

SILICONE POLYETHER ELASTOMER GELS

CROSS REFERENCE TO RELATED APPLICATIONS

This application is a U.S. national stage filing under 35 U.S.C. §371 of PCT Application No. PCT/US07/006,833 filed on Mar. 20, 2007, currently pending, which claims the benefit of U.S. Patent Application Ser. No. 60/784,340 filed on 21 Mar. 2006, U.S. Patent Application Ser. No. 60/799,864 filed on 12 May 2006 and U.S. Patent Application Ser. No. 60/838,802, filed on 18 Aug. 2006, under 35 U.S.C. §119(e).

TECHNICAL FIELD

This invention relates to gel compositions containing a silicone polyether elastomer from the reaction of an organohydrogensiloxane having at least two SiH containing cyclosiloxane rings in its molecule, a compound having at least two aliphatic unsaturated hydrocarbon groups in its molecule, and a hydrosilylation catalyst. The silicone polyether elastomer reaction product may itself be a gelled composition, or optionally may be contained in a carrier fluid to form a gel. The gel compositions may further contain a personal or healthcare active.

BACKGROUND

Silicone elastomers have been used extensively in personal care applications for their unique silky and powdery sensory profile. Most of these elastomers can gel volatile silicones fluids as well as low polarity organic solvents such as isododecane. Representative examples of such silicone elastomers are taught in U.S. Pat. Nos. 5,880,210, and 5,760,116. To improve compatibilities of silicone elastomers with various personal care ingredients, alkyls, polyether, amines or other organofunctional groups have been grafted onto the silicone elastomer backbone. Representative of such organofunctional silicone elastomers are taught in U.S. Pat. Nos. 5,811,487, 5,880,210, 6,200,581, 5,236,986, 6,331,604, 6,262,170, 6,531,540, and 6,365,670. Many of these silicone elastomers have limited compatibilities with various personal care ingredients, personal care actives and healthcare actives. These elastomers loose thickening and gelling efficiency, and even sensory benefits in the presence of personal care ingredients, personal care actives and healthcare actives. There is a need to further improve compatibilities of silicone elastomers with various personal care ingredients and actives.

However, there is still a need to further improve the efficiency of gelling volatile cosmetic fluids such as volatile silicones by silicone elastomers, and in particular to improve the rheological thickening effects by the addition of silicone elastomers to volatile cosmetic fluids. Furthermore, additional benefits are also sought for gelled compositions, such as improving the clarity of gelled silicone compositions and/or improved aesthetics upon application on skin.

The present inventors have discovered that silicone elastomers derived from cyclic organohydrogensiloxanes provide gelled compositions efficiently. The resulting gelled compositions also possess additional benefits, such as improved aesthetics and improved compatibilities with personal care ingredients and actives.

SUMMARY

This disclosure relates to a gel composition comprising a silicone polyether elastomer from the reaction of;

A) an organohydrogensiloxane having at least two SiH containing cyclosiloxane rings in its molecule
B) a compound or mixture of compounds having at least two aliphatic unsaturated hydrocarbon groups in its molecule,
C) a hydrosilylation catalyst,
and;
D) an optional carrier fluid;
with the proviso that at least 10 weight % of B) is an polyether compound.

This disclosure further relates to a process for preparing a silicone polyether elastomer gel containing an active comprising:
I) reacting;
 a) an organohydrogencyclosiloxane having at least two SiH units on a siloxane ring,
 B) a compound or mixture of compounds having at least two aliphatic unsaturated hydrocarbon groups in its molecule,
 C) a hydrosilylation catalyst
  with the proviso that at least 10 weight % of B) is an polyether compound to form
 A) an organohydrogensiloxane having at least two SiH containing cyclosiloxane rings in its molecule,
 wherein the molar ratio of the SiH units of component a) to the aliphatic unsaturated groups of component B) ranges from 2/1 to 8/1,
II) further reacting;
 A) the organohydrogensiloxane having at least two SiH containing cyclosiloxane rings in its molecule, with additional quantities of
 B) the compound or mixture of compounds containing at least two aliphatic unsaturated groups in its molecules,
 C) the hydrosilylation catalyst,
in the presence of
 D) an optional carrier fluid, and
 E) a personal care or healthcare active,
to form the silicone polyether elastomer gel.

A personal care or healthcare active may be incorporated into the silicone polyether elastomer gel by having it be present during the formation of the silicone polyether elastomer gel (pre-load method) or admixing it with a formed silicone polyether elastomer gel (post-load method).

DETAILED DESCRIPTION (A) The Organohydrogensiloxane Having at Least Two SiH Containing Cyclosiloxane Rings Component (A) in the present invention is an organohydrogensiloxane having at least two SiH containing cyclosiloxane rings in its molecule. Organohydrogensiloxanes suitable as component A) in the present invention are any organopolysiloxanes having in its molecule at least two cyclosiloxane rings with at least one silicon bonded hydrogen (SiH) unit on each siloxane ring. Organopolysiloxanes are well known in the art and are often designated as comprising any number of $(R_3SiO_{0.5})$, $(R_2SiO)$, $(RSiO_{1.5})$, or $(SiO_2)$ siloxy units where R is independently any organic group. When R is methyl in the siloxy unit formulas of an organopolysiloxane, the respective siloxy units are often designated as M, D, T or Q siloxy units. Cyclosiloxane rings contain at least three siloxy units (that is the minimum needed in order to form a siloxane ring), and may be any combination of $(R_3SiO_{0.5})$, $(R_2SiO)$, $(RSiO_{1.5})$, or $(SiO_2)$ siloxy units that forms a cyclic structure, providing at least one of the cyclic siloxy units on each siloxane ring contains one SiH unit, that is there is at least one $(R_2HSiO_{0.5})$, $(RHSiO)$, or a $(HSiO_{1.5})$ siloxy unit present in the ring. These siloxy units can be represented as $M^H$, $D^H$, and $T^H$ siloxy units respectively when R is methyl.

The cyclosiloxane rings of A) the organohydrogensiloxane are linked together by a divalent organic or siloxane group, or combination thereof. The divalent linking group may be designated as Y and the cyclosiloxane as G. Thus, the organohydrogensiloxane of the present invention may be represented by the general formula $G\text{-}[Y\text{-}G]_a$, where G is a cyclosiloxane as described above and Y is a divalent organic, a siloxane, a polyoxyalkylene group, or combination thereof, and the subscript a is greater than zero.

When Y is a divalent organic, it may be a divalent hydrocarbon containing 1 to 30 carbons, either as aliphatic or aromatic structures, and may be branched or un-branched. Alternatively, Y can be an alkylene group containing 2 to 20 carbons, or alternatively containing 4 to 12 carbons.

When Y is a divalent organic, it may also be selected from an organic polymer, such as a polyoxyalkylene group.

When Y is a siloxane group it may be selected from any organopolysiloxane containing at least two divalent hydrocarbon groups, designated as $R^1$. Thus, the siloxane linking group can be any organopolysiloxane comprising at least two siloxane units represented by the average formula $R^1R_m SiO_{(4-m)/2}$
wherein
R is an organic group,
$R^1$ is a divalent hydrocarbon, and
m is zero to 3

The $R^1$ group may be present on any mono, di, or tri-siloxy unit in an organopolysiloxane molecule, for example; $(R^1R_2SiO_{0.5})$, $(R^1RSiO)$, or $(R^1SiO_{1.5})$, as well as in combination with other siloxy units not containing an $R^1$ substituent, such as $(R_3SiO_{0.5})$, $(R_2SiO)$, $(RSiO_{1.5})$, or $(SiO_2)$ siloxy units where R is independently any organic group providing there are at least two $R^1$ substituents in the organopolysiloxane. Representative $R^1$ groups include; ethylene, propylene, butylene, isobutylene, hexylene, and similar homologs. Alternatively, $R^1$ is ethylene.

Representative, non-limiting, examples of such siloxane based structures suitable as siloxane linking groups include;

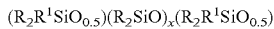

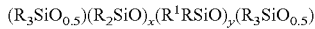

where $x \geq 0$, $y \geq 2$, and z is $\geq 0$

Organohydrogensiloxane having at least two SiH containing cyclosiloxane rings (component A) may be prepared via a hydrosilylation reaction of a) an organohydrogencyclosiloxane having at least two SiH units on the siloxane ring and, B) a compound or mixture of compounds having at least two aliphatic unsaturated groups in its molecule.

The organohydrogencyclosiloxane (a) having at least two SiH units on the siloxane ring may contain any number of siloxy units (as defined above) provided there are at least two SiH units on the cyclosiloxane ring. For example, the cyclic siloxane can comprise any number of M, $M^H$, D, $D^H$, or $T^H$ siloxy units. Representative, non-limiting examples of such organohydrogencyclosiloxanes useful to prepare component (A) have the average formula $D^H_a D_b$ where a is $\geq 1$ and b is $\geq 0$, and $a+b \geq 3$. Alternatively, the organohydrogencyclosiloxane may be selected from those having the formula $[(CH_3)HSiO]_g$ where g is 3-8, such as $D^H_4$, $D^H_5$, $D^H_6$, or mixtures thereof.

Suitable compounds containing at least two aliphatic unsaturated hydrocarbon groups in its molecule are described below as component B).

Hydrosilylation reactions involving organohydrogensiloxanes and unsaturated compounds are well known. Any suitable hydrosilylation catalysts know in the art may be used, or alternatively may be selected from those described below as component C). Any of the known hydrosilylation techniques and reactions may be employed to prepare component A) from i) organohydrogencyclosiloxane having at least two SiH units on the siloxane ring and, B) a compound or mixture of compounds having at least two aliphatic unsaturated groups in its molecule. However, the reaction is conducted in such a manner to provide an organohydrogensiloxane having at least two SaH containing cyclosiloxane rings in its molecule.

Thus, component A of the present invention contains at least two silicon-bonded hydrogen atom per molecule, alternatively at least 4 silicon-bonded hydrogen atoms per molecule, or alternatively at least 6 silicon-bonded hydrogen atoms per molecule. This can be accomplished by using in the hydrosilylation reaction a molar excess of the a) the organohydrogencyclosiloxane having at least two SiH units on the siloxane ring vs. the compound containing at least two aliphatic unsaturated groups in its molecule. The molar excess may be expressed as the molar ratio of SiH units to unsaturated group, such ratio may range from 2/1 to 8/1, alternatively from 2/1 to 6/1, or alternatively from 3/1 to 4/1.

Alternatively, the organohydrogensiloxane useful as component A) may be selected from any of the organohydrogensilocanes taught in WO03/093349, which is herein incorporated by reference for its teaching of suitable organohydrogensiloxanes.

The organohydrogensiloxane useful as component A) in the present invention typically have a viscosity from 5 to 50,000 mPa·s, alternatively from 10 to 10,000 mPa·s, or alternatively from 25 to 2,000 mPa·s.

Representative, non-limiting examples of component A) include;

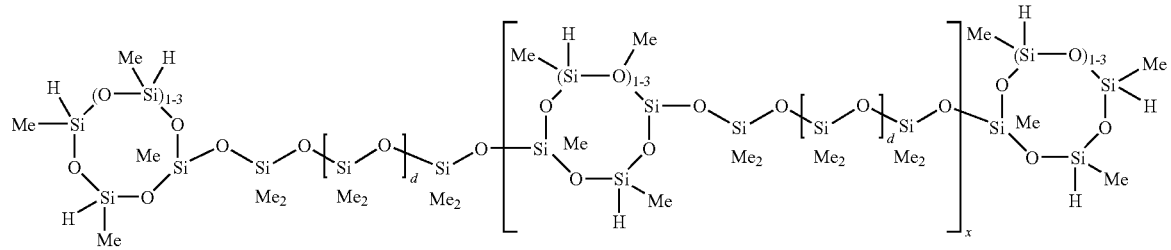

-continued

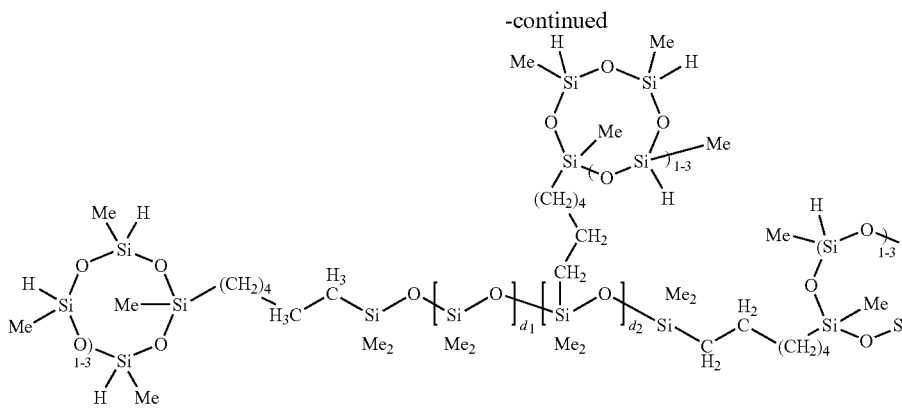

Additives known as inhibitors or stabilizers may be added to component A). Inhibitors such as those described in WO 03/093369 may be added for the purpose of stabilizing component A) during storage, or prior to the addition of component B) to prepare the silicone elastomer gel. The inhibitor may be selected from any compound known to have inhibiting effects of platinum based hydrosilylation reactions. Examples of known inhibitors include triphenyl phosphate, tocopherol (vitamin E), and butylated hydroxy toluene. A particularly preferred inhibitor is vitamin A palmitate, or VAP. When VAP is used, it is typically added at 0.05 to 2.0 parts per 100 parts of component A).

(B) The Compound or Mixture of Compounds Having at Least Two Aliphatic Unsaturated Hydrocarbon Grows in its Molecule Component (B) is a compound, or any mixture of compounds, containing at least two aliphatic unsaturated groups in its molecule. The compound may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^2$—Y—$R^2$ where $R^2$ is a monovalent unsaturated aliphatic hydrocarbon group containing 2 to 12 carbon atoms, and Y is a divalent organic or siloxane group or a combination of these. Typically $R^2$ is $CH_2$=CH—, $CH_2$=CHCH$_2$—, $CH_2$=CH(CH$_2$)$_4$—, $CH_2$=C(CH$_3$)CH$_2$— or CH≡C—, and similar substituted unsaturated groups such as $H_2C$=C(CH$_3$)—, and HC≡C(CH$_3$)—.

The compound having the formula $R^2$—Y—$R^2$ as component B) may be considered as being a "organic", "hydrocarbon", "organic polymer", "polyether" or "siloxane", or combinations thereof, depending on the selection of Y. Y may be a divalent hydrocarbon, a siloxane, a polyoxyalkylene, a polyalkylene, a polyisoalkylene, a hydrocarbon-silicone copolymer, or mixtures thereof.

In one embodiment, the component (B) is selected from an organic compound, herein denoted as (B$^1$), having the formula $R^2$—Y$^1$—$R^2$ where $R^2$ is a monovalent unsaturated aliphatic group containing 2 to 12 carbon atoms and Y$^1$ is a divalent hydrocarbon. The divalent hydrocarbon Y$^1$ may contain 1 to 30 carbons, either as aliphatic or aromatic structures, and may be branched or un-branched. Alternatively, the linking group Y$^1$ in B$^1$ may be an alkylene group containing 1 to 12 carbons. Component (B$^1$) may be selected from α, ω—un-saturated alkenes or alkynes containing 1 to 30 carbons, and mixtures thereof. Component (B$^1$) may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the component (B) is selected from a $R^2$—Y$^2$—$R^2$ compound where Y$^2$ is a siloxane, herein denoted as (B$^2$). The Y$^2$ siloxane group may be selected from any organopolysiloxane bonded to at least two organic groups having aliphatic saturation, designated as $R^2$, to form $R^2$—Y$^2$—$R^2$ structures. Thus, component (B$^2$) can be any organopolysiloxane, and mixtures thereof, comprising at least two siloxane units represented by the average formula $R^2R_mSiO_{(4-m)/2}$ wherein
R is an organic group,
$R^2$ is a monovalent unsaturated aliphatic group as defined above, and
m is zero to 3

The $R^2$ group may be present on any mono, di, or tri siloxy unit in an organopolysiloxane molecule, for example; $(R^2R_2SiO_{0.5})$, $(R^2RSiO)$, or $(R^2SiO_{1.5})$; as well as in combination with other siloxy units not containing an $R^2$ substituent, such as $(R_3SiO_{0.5})$, $(R_2SiO)$, $(RSiO_{1.5})$, or $(SiO_2)$ siloxy units where R is independently any organic group, alternatively a hydrocarbon containing 1 to 30 carbons, alternatively an alkyl group containing 1 to 30 carbons, or alternatively methyl; providing there are at least two $R^2$ substituents in the organopolysiloxane.

Representative, non-limiting, examples of such siloxane based $R^2$—Y$^2$—$R^2$ structures suitable as component (B$^2$) include;

$(R_2R^2SiO_{0.5})(SiO_2)_w(R_2R^2SiO_{0.5})$ $(R_2R^2SiO_{0.5})(SiO_2)_w(R_2SiO)_x(R_2R^2SiO_{0.5})$ $(R_2R^2SiO_{0.5})(R_2SiO)_x(R_2R^2SiO_{0.5})$ $(R_3SiO_{0.5})(R_2SiO)_x(R^2RSiO)_y(R_3SiO_{0.5})$ $(R_3SiO_{0.5})(R_2SiO)_x(R^2RSiO)_y(RSiO_{1.5})_z(R_3SiO_{0.5})$ $(R_3SiO_{0.5})(R_2SiO)_x(R^2RSiO)_y(SiO_2)_w(R_3SiO_{0.5})$ where w≧0, x≧0, y≧2, and z is 0, R is an organic group, and $R^2$ is a monovalent unsaturated aliphatic hydrocarbon group.

$B^2$ may be selected from vinyl functional polydimethylsiloxanes (vinyl siloxanes) or hexenyl functional polydimethylsiloxanes (hexenyl siloxanes), such as those having the average formula;

$CH_2=CH(Me)_2SiO[Me_2SiO]_xSi(Me)_2CH=CH_2$ $CH_2=CH-(CH_2)_4-(Me)_2SiO[Me_2SiO]_xSi(Me)_2-(CH_2)_4-CH=CH_2$ $Me_3SiO[(Me)_2SiO]_x[CH_2=CH(Me)SiO]_ySiMe_3$ wherein Me is methyl,
$x \geq 0$, alternatively x is 0 to 200, alternatively x is 10 to 150,
$y \geq 2$, alternatively y is 2 to 50, alternatively y is 2 to 10.
Vinyl functional polydimethylsiloxanes are known, and there are many commercially available.

In another embodiment, component (B) is selected from a polyether compound, herein denoted as $(B^3)$, having the formula $R^2-Y^3-R^2$ compound where $R^2$ is as defined above and $Y^3$ is a polyoxyalkylene group having the formula $(C_nH_{2n}O)_b$ wherein n is from 2 to 4 inclusive, b is greater than 2,
alternatively b can range from 2 to 200,
or alternatively b can range from 2 to 100.

The polyoxyalkylene group typically can comprise oxyethylene units $(C_2H_4O)$, oxypropylene units $(C_3H_6O)$, oxybutylene or oxytetramethylene units $(C_4H_8O)$, or mixtures thereof. Thus, the $R^2-Y^3-R^2$ compound may be selected from a polyoxyalkylene group having the formula $R^2-[(C_2H_4O)_c(C_3H_6O)_d(C_4H_8O)_e]-R^2$ where c, d, and e may each independently range from 0 to 200, providing the sum of c+d+e is greater than 2, alternatively the sum of c+d+e ranges from 2 to 200, or alternatively the sum of c+d+e ranges from 2 to 100.

Alternatively, the polyoxyalkylene group comprises only oxypropylene units $(CH_3H_6O)_d$. Representative, non-limiting examples of polyoxypropylene containing $R^2-Y^3-R^2$ compounds include;

$H_2C=CHCH_2[C_3H_6O]_dCH_2CH=CH_2$ $H_2C=CH[C_3H_6O]_dCH=CH_2$ $H_2C=C(CH_3)CH_2[C_3H_6O]_dCH_2C(CH_3)=CH_2$ $HC\equiv CCH_2[C_3H_6O]_dCH_2C\equiv CH$ $HC\equiv CC(CH_3)_2[C_3H_6O]_dC(CH_3)_2C\equiv CH$ where d is as defined above.
Representative, non-limiting examples of polyoxybutylene or poly(oxytetramethylene) containing $R^2-Y^3-R^2$ compounds include;

$H_2C=CHCH_2[C_4H_8O]_eCH_2CH=CH_2$ $H_2C=CH[C_4H_8O]_eCH=CH_2$ $H_2C=C(CH_3)CH_2[C_4H_8O]_eCH_2C(CH_3)=CH_2$ $HC\equiv CCH_2[C_4H_8O]_eCH_2C\equiv CH$ $HC\equiv CC(CH_3)_2[C_4H_8O]_eC(CH_3)_2C\equiv CH$ Component B) may also be a mixture of various polyethers, i.e. a mixture of $B^3$ components.

In another embodiment, component (B) is selected from a $R^2-Y^4-R^2$ compound, herein denoted as $(B^4)$, where $R^2$ is as defined above and $Y^4$ is a polyalkylene group, selected from C2 to C6 alkylene units or their isomers. One example is polyisobutylene group which is a polymer containing isobutylene unit. The molecular weight of the polyisobutylene group may vary, but typically ranges from 100 to 10,000 g/mole. Representative, non-limiting examples of $R^2-Y-R^2$ compounds containing a polyisobutylene group includes those obtained from BASF under the tradename of OPPONOL BV, such as OPPONOL BV 5K, a diallyl terminated polyisobutylene having an average molecular weight of 5000 g/mole.

In yet another embodiment, component (B) is selected from a $R^2-Y^5-R^2$ compound, herein denoted as $(B^5)$, where $R^2$ is as defined above and $Y^5$ is a hydrocarbon-silicone copolymer group. The hydrocarbon-silicone copolymer group may have the formula $-[R^1{}_u(R_2SiO)_v]_q-$ where $R^1$ and R are as defined above;
u and v are independently $\geq 1$, alternatively u ranges from 1 to 20,
alternatively v ranges from 2 to 500, or from 2 to 200,
q is $\geq 1$, alternatively q ranges from 2 to 500, alternatively q ranges from 2 to 100.
$R^2-Y^5-R^2$ compounds having a hydrocarbon-silicone copolymer group may be prepared via a hydrosilylation reaction between an α-ω unsaturated hydrocarbon, such as those described above as $B^1$, and an organohydrogensiloxane. A representative, non-limiting example of such a reaction is shown below.

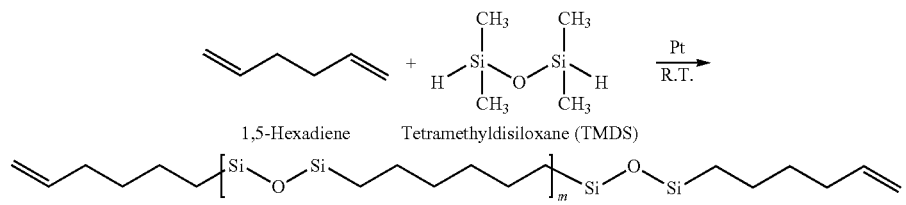

Component (B) may also be a mixture of any diene, diyne or ene-yne compound, such as any combinations of $B^1$, $B^2$, $B^3$, $B^4$, and $B^5$.

The amounts of component (A) and component (B) used to prepare the present composition will depend on the individual components and the desired SiH to aliphatic unsaturation ratio. The ratio of SiH in component (A) to aliphatic unsaturation from component (B) useful to prepare the compositions of the present invention can be from 10:1 to 1:10, alternatively 5:1 to 1:5, or alternatively 4:1 to 1:4.

If components (A) and (B) are not the only materials containing aliphatic unsaturated groups and SiH-containing groups in the present composition, then the above ratios relate to the total amount of such groups present in the composition rather than only those components.

(C) The Hydrosilylation Catalyst
Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(Si/MeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

(D) The Carrier Fluid

The silicone elastomers may be contained in an optional carrier fluid (D). Although it is not required, typically the carrier fluid may be the same as the solvent used for conducting the hydrosilylation reaction as described above. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 $mm^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsily)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H (C11-C12), hydrogentated polydecen. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME). octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 90 weight percent, alternatively 5 to 80 weight percent, of carrier fluid in composition containing (A) and (B) and (D), where the sum of (A), (B), and (D) is 100 weight percent.

E) Personal or Healthcare Active

Component E) is active selected from any personal or health care active. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Thus, active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of active ingredients include; drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in processes according to the invention include vitamins and its derivatives, including "pro-vitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

RETINOL, it should be noted, is an International Nomenclature Cosmetic Ingredient Name (INCI) designated by The Cosmetic, Toiletry, and Fragrance Association (CTFA), Washington DC, for vitamin A. Other suitable vitamins and the INCI names for the vitamins considered included herein are RETINYL ACETATE, RETINOL PALMITATE, RETINOL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active component E) of the present invention can be a protein, such as an enzyme. The internal inclusion of enzymes in the silicone elastomer gel have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

Component E) may also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bomelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

Component E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as *Perfume and Flavour Chemicals,* 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbomane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahrdro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl) propanal, dihydrocinnamaldehyde, 1-methyl-4-(4-methyl-3-pentenyl)-3-cyclohexene-1-carbox aldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena 1, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P. T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

Component E) may also be one or more plant extract. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric [Curcuma] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, Saponaria extract, Bamboo extract, Crataegus fruit extract, Zanthoxylum fruit extract, shiitake extract, Rehmannia root extract, gromwell extract, Perilla extract, linden extract, Filipendula extract, peony extract, Calamus Root extract, white birch extract, Horsetail extract, Hedera Helix (Ivy) extract, hawthorn extract, Sambucus nigra extract, Achillea millefolium extract, Mentha piperita extract, sage extract, mallow extract, Cniditum officinale Root extract, Japanese green gentian extract, soybean extract, jujube extract, thyme extract, tea extract, clove extract, Gramineae imperata cyrillo extract, Citrus unshiu peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extract, Nelumbo nucifera extract, parsley extract, honey, hamamelis extract, Parietaria extract, Isodonis herba extract, bisabolol extract, Loquat extract, coltsfoot extract, butterbur extract, Porid cocos wolf extract, extract of butcher's broom, grape extract, propolis extract, luffa extract, safflower extract, peppermint extract, linden tree extract, Paeonia extract, hop extract, pine tree extract, horse chestnut extract, Mizu-bashou [Lysichiton camtschatcese] extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

The amount of component E) present in the silicone gel composition may vary, but typically range as follows;

0.05 to 50 wt %, alternatively 1 to 25 wt %, or alternatively 1 to 10 wt %, based on the amount by weight of silicone elastomer gel present in the composition, that is total weight of components A), B), C) and D) in the silicone gel composition.

The active, component E), may be added to the silicone gel composition either during the malting of the silicone elastomer (pre-load method), or added after the formation of the silicone elastomer gel (post load method).

The pre-load method involves;
I) reacting;
  a) an organohydrogencyclosiloxane having at least two SiH units on a siloxane ring,
  B) a compound or mixture of compounds having at least two aliphatic unsaturated hydrocarbon groups in its molecules,
  C) a hydrosilylation catalyst,
    with the proviso that at least 10 weight % of B) is a polyether compound, to form
  A) an organohydrogensiloxane having at least two SiH containing cyclosiloxane rings in its molecule,
  wherein the molar ratio of the SiH units of component a) to the aliphatic unsaturated hydrocarbon groups of component B) ranges from 2/1 to 8/1,
II) reacting;
  A) the organohydrogensiloxane having at least two SiH containing cyclosiloxane rings in its molecule, with additional quantities of
  B) the compound containing at least two aliphatic unsaturated hydrocarbon groups in its molecules,
  C) the hydrosilylation catalyst,
in the presence of
  D) an optional carrier fluid, and
  E) a personal care or healthcare active,
to form the silicone polyether elastomer gel.

The post-load method involves;
I) reacting;
  a) an organohydrogencyclosiloxane having at least two SiH units on a siloxane ring,
  B) a compound or mixture of compounds having at least two aliphatic unsaturated groups in its molecules,
  C) a hydrosilylation catalyst
    with the proviso that at least 10 weight % of B) is a polyether compound, to form
  A) an organohydrogensiloxane having at least two SiH containing cyclosiloxane rings in its molecule,
  wherein the molar ratio of the SiH units of component a) to the aliphatic unsaturated groups of component B) ranges from 2/1 to 8/1,
II) further reacting;
  A) the organohydrogensiloxane having at least two SiH containing cyclosiloxane rings in its molecule, with additional quantities of
  B) the compound containing at least two aliphatic unsaturated groups in its molecules,
  C) the hydrosilylation catalyst,
in the presence of
  D) an optional carrier fluid
to form a silicone elastomer gel,
III) admixing
  E) a personal care or healthcare active with the silicone elastomer gel to form the silicone elastomer gel containing active.

The Silicone Elastomer

The silicone elastomers of the present invention are obtainable as hydrosilylation reaction products of components A), B), and C). The term "hydrosilylation" means the addition of an organosilicon compound containing silicon-bonded hydrogen, (such as component A) to a compound containing aliphatic unsaturation (such as component B), in the presence of a catalyst (such as component C). Hydrosilylation reactions are known in the art, and any such known methods or techniques may be used to effect the hydrosilylation reaction of components A), B), and C) to prepare the silicone elastomers of the present invention.

The hydrosilylation reaction may be conducted in the presence of a solvent, and the solvent subsequently removed by known techniques. Alternatively, the hydrosilylation may be conducted in a solvent, where the solvent is the same as the carrier fluid described as optional component D).

Alternatively, the silicone elastomers may be prepared by a process comprising:
I) reacting;
  a) an organohydrogencyclosiloxane having at least two SiH units on a siloxane ring,
  B) a compound containing at least two aliphatic unsaturated groups in its molecules,
  C) a hydrosilylation catalyst,
    with the proviso that at least 10 weight % of B) is a polyether compound to form
  A) an organohydrogensiloxane having at least two SiH containing cyclosiloxane rings in its molecule,
wherein the molar ratio of the SiH units of component a) to the aliphatic unsaturated groups of component B) ranges from 2/1 to 8/1,
  alternatively from 2/1 to 6/1,
  or alternatively from 3/1 to 4/1,
II) further reacting;
  A) the organohydrogensiloxane having at least two SiH containing cyclosiloxane rings in its molecule, with additional quantities of
  B) the compound containing at least two aliphatic unsaturated groups in its molecules,
  C) the hydrosilylation catalyst.
to form a silicone elastomer.

Components a, A), B), C) are the same as those described above. Also, the reaction may be conducted under similar conditions as described above.

In aforementioned step II) the molar ratio of the SiH units of component A) to the aliphatic unsaturated groups of component B) ranges from 10/1 to 1/10,
  alternatively from 5/1 to 1/5,
  or alternatively from 4/1 to 1/4, Gelled Compositions Containing the Silicone Elastomer The silicone elastomers can be added to a carrier fluid (as described above as component D) to form gelled compositions, or alternatively be prepared first in a separate reaction and then added to the carrier fluid to obtain a gel. The gelled compositions of the present invention may be characterized by their hardness or firmness. Useful tests to characterize the gels are those recommended by the *Gelatin Manufacturers Institute of America* such as the use of a "Texture Analyzer" (model TA.XT2, Stable Micro Systems, Inc., Godalming, England). The gel sample is subject to a compression test with the Texture Analyzer having a probe with a 5.0 kg load cell. The probe approaches the surface of the gel at a speed of 0.5 mm/sec and continues compression into the gel to a distance of 5.0 mm, then holds for 1 second before retreating. The Texture Analyzer detects the resistance force the probe experiences during the compression test. The force exhibited by the load cell is plotted as a function of time.

The hardness of the silicone elastomers, gels and elastomer blends (SEBs) for purposes of this invention is defined as the resistance force detected by the probe of the "Texture Analyzer" during the compression test. Two data may used to characterize hardness: Force 1, the force at the maximum compression point (i.e. the 5.0 mm compression point into the gel surface), and Area F-T: the area-force integration during the 1 second hold at the maximum compression point. The average of a total of 5 tests are typically performed for each gel.

The value obtained for Force 1 is converted into Newton (N), by dividing the gram force value by 101.97. (i.e. 1 Newton equals 101.97 g force based on the size of the probe used in this instrument). The second property reported by Texture Analyzer measurement is Area F-T 1:2, in g force·sec. This is the area integration of the force vs. test time cure. This property is indicative of a gel network since it indicates ability to sustain resistance to the compression force, which is relevant to elastomers and gels. The value is reported in g force·sec, and is converted to Newton·sec in SI unit by dividing the value in g force·sec by 101.97.

The silicone gels of the present invention has a compression hardness of at least 200 Newton/m$^2$, alternatively 400 Newton/m$^2$, or alternatively 600 Newton/m$^2$.

Gel Paste Compositions Containing the Silicone Elastomer

The gelled compositions of the present invention can be used to prepare gel paste compositions containing actives by;

I) shearing the silicone polyether elastomer gel, as described above,

II) combining the sheared silicone polyether elastomer gel with additional quantities of D) the carrier fluid, as described above, and E) a personal or health care active active to form a gel paste composition.

The silicone polyether elastomer gel compositions of the present invention blends may be considered as discrete crosslinked silicone elastomer gel particles dispersed in carrier fluids. Thus, the silicone elastomer compositions are effective rheological thickeners for lower molecular weight silicone fluids. As such they can be used to prepare useful gel blend compositions, such as "paste" compositions.

To make such silicone elastomer blends, the aforementioned silicone elastomer gels of known initial elastomer content (IEC) are sheared to obtain small particle size and further diluted to a final elastomer content (FEC). "Shearing", as used herein refers to any shear mixing process, such as obtained from homogenizing, sonalating, or any other mixing processes known in the art as shear mixing. The shear mixing of the silicone elastomer gel composition results in a composition having reduced particle size. The subsequent composition having reduced particle size is then further combined with D) the carrier fluid. The carrier fluid may be any carrier fluid as described above, but typically is a volatile methyl siloxane, such as D5. The technique for combining the D) the carrier fluid with the silicone elastomer composition having reduced particle size is not critical, and typically involves simple stirring or mixing. The resulting compositions may be considered as a paste, having a viscosity greater than 100,000 cP (mPa·s).

EXAMPLES

These examples are intended to illustrate the invention to one of ordinary skill in the art and are should not be interpreted as limiting the scope of the invention set forth in the claims.

Materials Description

The following materials were used in these examples.

Organohydrogensiloxanes

MeH CYCLICS=methylhydrogen cyclosiloxanes (MeH cyclics) having the formula $[(CH_3)HSiO]_x$ where the average value of x is 4.4.

MeH LINEAR=an organohydrogenpolysiloxane have the average formula $MD_{94}D'_6M$ Siloxane Polymers Containing Unsaturated Groups VINYL SILOXANE #1=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 8 and having a viscosity of 4 mm$^2$/s at 25° C.

VINYL SILOXANE #2=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 130 and having a viscosity of 325 mm$^2$/s at 25° C.

VINYL SILOXANE #3=$[(CH_2=CH)(CH_3)_2SiO[(CH_3)_2SiO]_{30}]_4Si$

VINYL SILOXANE #4=tetramethyltetravinylcyclotetrasiloxane $[(CH_2=CH)(CH_3)SiO]_4$ VINYL SILOXANE #5=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 27 and having a viscosity of 25 mm$^2$/s at 25° C.

VINYL SILOXANE #6=a dimethylhexenylsiloxy-terminated dimethylpolysiloxane of the general formula $(CH_2=CH(CH_2)_4)(CH^3)_2SiO[(CH_3)_2SiO]_{dp}Si(CH_3)_2((CH_2)_4(CH_2=CH))$, where the average degree of polymerization (dp) was 37 and a viscosity of 40 mm$^2$/s at 25° C.

VINYL SILOXANE #7=a dimethylhexenylsiloxy-terminated dimethylpolysiloxane of the general formula $(CH_2=CH(CH_2)_4)(CH_3)_2SiO[(CH_3)_2SiO]_{dp}Si(CH_3)_2((CH_2)_4(CH_2=CH))$, where the average degree of polymerization (dp) was 100 and a viscosity of 170 mm$^2$/s at 25° C.

VINYL SILOXANE #8=a dimethylhexenylsiloxy-terminated dimethylpolysiloxane of the general formula $(CH_2=CH(CH_2)_4)(CH_3)_2SiO[(CH_3)_2SiO]_{dp}Si(CH_3)_2((CH^2)_4(CH_2=CH))$, where the average degree of polymerization (dp) was 200 and a viscosity of 730 mm$^2$/s at 25° C.

VINYL SILOXANE #9=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 130 and having a viscosity of 300 mm$^2$/s at 25° C.

VINYL SILOXANE #10=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 27.

α,ω-Unsaturated Polypropylene Oxide

PO20-Polycerin DUS-80=α,ω-diallyl polypropylene oxide having 20 propylene oxide (PO) units from NOF Corporation (Japan).

PO50-Unisafe PKA-5018=α,ω-diallyl polypropylene oxide having 50 propylene oxide (PO) units from NOF Corporation (Japan).

Hydrosilylation Catalyst

PT CATALYST=SLY-OFF 4000 (Dow Corning Corporation, Midland Mich.) Pt catalyst used as provided containing 0.52 weight % Pt.

Carrier Fluids

D5=decamethylcyclopentasiloxane or D5 cyclics, DC245 (Dow Corning Corporation, Midland Mich.) used as provided.

IDNP=isodecyl neopentanoate obtained from ISP (International Specialty Products Co) under the trade name of CERAPHYL SLK.

IDD=isododecane

Stabilizer=Vitamin A palmitate (VAP) and butylated hydroxytoluene (BHT)

Methods of Measuring Viscosity of Silicone Elastomer Blends (SEBs)

The Brookfield Helipath™ Stand, when used with a suitable Brookfield Viscometer fitted with a special T-bar type spindle, will permit viscosity/consistency measurements in relative centipoise values for materials having characteristics similar to paste, putty, cream, gelatin, or wax.

The viscosity of silicone elastomer blends was determined using a Brookfield Model RVD-II+ Viscometer with Helipath stand (Brookfield Model D) and T-Bar spindles (Brookfield Helipath Spindle Set). All were purchased from Brookfield Engineering Laboratories, Inc. (11 Commerce Boulevard Middleboro, Mass., USA).

A sample size of 100 g in a 4 oz. round jar was required. The following preparation procedure was used before measurement: the sample was de-aired first via centrifuge, then vacuum de-aired for two hours. After de-airing, the sample was conditioned for a minimum of 4 hours @25° C. The sample was positioned with T-bar spindle at center. The reading was taken according to the typical procedure for Helipath spindle.

In general, spindle 93 (1"-bar spindle C) is used for the less viscous sample, spindle 95 (T-bar spindle E) for the more viscous samples. The standard setting for rpm was 2.5. The spindle speed is maintained at constant 2.5 rpm and spindle was varied to handle samples with significant viscosities.

Measurement of Silicone Elastomer Gel Hardness

The hardness (or firmness) of silicone elastomer gels was characterized using a Texture analyzer (model TA.XT2, Stable Micro Systems, Inc., Godalming, England). The *Gelatin Manufacturers Institute of America* recommends such test methods as a standard procedure.

For silicone gels and elastomer blends, a ½ inch (1.27 cm) diameter cylindrical probe made of DELRIN acetal resin (Dupont) was used for the measurement. The gel sample is subject to the compression test using the probe with the following test cycle: the probe approaches the surface of the gel at a speed of 0.5 mm/sec and continues compression into the gel to a distance of 5.0 mm, then holds for 1 second before retreating. The Texture Analyzer has a 5.0 Kg load cell to detect the resistance force the probe experiences during the compression test.

The force exhibited by the load cell is plotted as a function of time.

The hardness of the silicone elastomers, gels and elastomer blends (SEBs) is defined as the resistance force detected by the probe during the compression test. Two data are used for the hardness value: Force 1: the force at the maximum compression point (i.e. the 5.0 mm compression point into the gel surface), and Area F-T: the area-force integration during the 1 second hold at the maximum compression point. A total of 5 tests were performed for each gel and the average of the five tests is reported.

Texture Analyzer used for gel hardness measurement is force in gram, as detected by the transducer. Two values are reported for gel hardness: Force 1, the force in gram registered when the probe reached its pre-programmed full indentation (or compression) in gel sample. The unit for Force 1 reading is gram force.

The value obtained for Force 1 is converted into Newton (N), by dividing the gram force value by 101.97. (i.e. 1 Newton equals 101.97 g force based on the size of the probe used in this instrument). For instance, a value of 6327 g force converts to 62.0 N.

The second property reported by Texture Analyzer measurement is Area F-T 1:2, in g force·sec. This is the area integration of the force vs. test time cure. This is an indicative property of a gel network as it indicates it ability to sustain resistance to the compression force, which is relevant to elastomers and gels.

The value is reported in g force·sec, and is converted to Newton·sec in SI unit by dividing the value in g force·sec by 101.97. For instance, a value of 33,947 g force·sec is 332.9 N·s in SI units.

Example 1

Reference

Preparation of an Organohydrogensiloxane Having at Least Two SiH Containing Cyclosiloxane Rings Organohydrogensiloxanes illustrative as component A) were prepared from MeH CYCLICS and VINYL SILOXANE #7. The organohydrogensiloxane intermediates were made to about 50 wt. % in D5 fluid, IDNP (isodecyl neopentanoate), and IDD (isododecane), respectively. The details of these organohydrogensiloxanes are shown in Table 1.

TABLE 1

Composition of organohydrogensiloxane

| | Example # | | |
|---|---|---|---|
| | 1A | 1B | 1C |
| SiH:Vi ratio | 3.42 | 3.42 | 3.42 |
| Compound B) | $M^{hex}D_{100}M^{hex}$ | $M^{hex}D_{100}M^{hex}$ | $M^{hex}D_{100}M^{hex}$ |
| | VINYL SILOXANE #7 | VINYL SILOXANE #7 | VINYL SILOXANE #7 |
| % Component A in mixture | 50.0 | 50.0 | 50.0 |

TABLE 1-continued

Composition of organohydrogensiloxane

| | Example # | | |
|---|---|---|---|
| | 1A | 1B | 1C |
| Carrier fluid type | D5 fluid | Isodecyl Neopentanoate | Isododecane |
| Wt. % H, theoretical Actual amount | 0.0289 | 0.0289 | 0.0289 |
| MeH CYCLICS, g | 14.79 | 14.79 | 14.790 |
| $M^{hex}D_{100}M^{hex}$ VINYL SILOXANE #7, g | 285.23 | 285.22 | 285.36 |
| D5 fluid, g | 300.00 | | |
| Isodecyl Neopentanoate (IDNP), g | | 300.04 | |
| Isododecane (IDD), g | | | 300.0 |
| Sly-Off 4000 catalyst | 0.35 | 0.35 | 0.35 |
| Stabilizer (VAP/BHT @ 98.5/1.5 w/w), g | 4.0 | 3.1 | 3.10 |
| Total Batch, g | 604.37 | 603.50 | 603.61 |
| Mixture appearance | Clear, slightly yellowish mixture | Clear yellowish mixture | Clear, slightly yellow mixture |

These organohydrogensiloxanes were made by charging MeH CYCLICS, VINYL SILOXANE #7, and the corresponding carrier fluid into a reaction flask, mixed to homogeneous. Then the mixture was catalyzed with 3-5 ppm of Pt (Sly-Off 4000 Pt catalyst solution containing 0.52 wt % Pt). The mixture was heated to 50° C. to causing an exothermic hydrosilylation reaction to occur, the temperature was then maintained between 50 and 70° C. for 3 hours. Then, 0.5 to 0.75% of VAP/BHT (vitamin A palmitate and butylated hydroxytoluene) stabilizer was incorporated once the reaction mixture cooled to below 40° C.

These organohydrogensiloxanes were made by charging McH CYCLICS, VINYL SILOXANE #7, and the corresponding carrier fluid into a reaction flask, mixed to homogeneous. Then the mixture was catalyzed with 3-5 ppm of Pt (Sly-Off 4000 Pt catalyst solution containing 0.52 wt % Pt). The mixture was heated to 50° C. to causing an exothermic hydrosilylation reaction to occur, the temperature was then maintained between 50 and 70° C. for 3 hours. Then, 0.5 to 0.75% of VAP/BHT (vitamin A palmitate and butylated hydroxytoluene) stabilizer was incorporated once the reaction mixture cooled to below 40° C.

Example 2

Reference

Preparation of an Organohydrogensiloxane Having at Least Two SiH Containing Cyclosiloxane Rings and Having Branched Structures Cyclic SiH-containing siloxanes having branched structure were also made. These siloxanes were made by reacting MeH CYCLICS with dimethyvinyl-ended branched silicones or methyvinyl cyclics. Detailed in Table 2 are the examples derived from VINYL SILOXANE #3 and VINYL SILOXANE #4. The [SiH]/[Vi] molar ratio was between 3.42 and 4.0 for these three examples and the reaction was carried out at 40° C. The resulting organohydrogensiloxanes were clear liquids with the average structures as shown Table 2. The content of cyclic SiH functionality in these siloxanes was 0.241%, 0.290%, and 0.376% respectively.

TABLE 2

SiH-functional cyclosiloxane having branched structures

| | Example # | | |
|---|---|---|---|
| | 2A | 2B | 2C |
| SiH:Vi ratio | 3.415 | 4.000 | 3.415 |
| Vinyl extender type | VINYL SILOXANE #3 | VINYL SILOXANE #3 | VINYL SILOXANE #4 |
| Target structure | 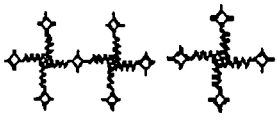 | 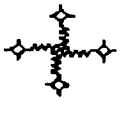 | 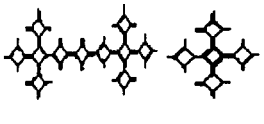 |
| % Component A in mixture | 100.0 | 100.0 | 100.0 |
| Wt. % H, theoretical Actual amount | 0.241 | 0.290 | 0.376 |
| MeH CYCLICS, g | 41.156 | 46.563 | 64.175 |
| 2-7754 Q-vinyl, g | 158.85 | 153.43 | |
| 1-2287 cyclics, g | | | 135.82 |
| Sly-Off 4000, g | 0.160 | 0.160 | 0.160 |

TABLE 2-continued

SiH-functional cyclosiloxane having branched structures

| | Example # | | |
|---|---|---|---|
| | 2A | 2B | 2C |
| Total Batch, g | 200.17 | 200.15 | 200.16 |
| Mixture appearance | Clear, viscous liquid | Clear, viscous liquid | Clear liquid with moderate viscosity |

Example 3

Reference

Preparation of an Organohydrogensiloxane Having at Least Two SiH Containing Cyclosiloxane Rings and Polyoxyalkylene Spacer Groups A polyoxyalkylene containing organohydrogensiloxane (component A) was prepared by reacting MeH CYCLICS with an α,ω-diallyl poly(alkyleneoxide) polyether, neat or in a carrier fluid, in the presence of Pt catalyst with added stabilizer using the same procedure as described in Example 1. The amounts used are summarized in Table 3.

TABLE 3

| | Example # 3 |
|---|---|
| SiH:Vi ratio | 3.415 |
| Vinyl extender type | Polycerin DUS-80 PO20 polyether |
| Wt. % Organics in component A) | 75.4 |
| Wt. % component A) in mixture | 50.0 |
| Wt. % SiH (theoretical) Theoretical amount | 0.1445 |
| MH-1109, g | 36.950 |
| PO20, Polycerin DUS-80 g | 113.050 |
| IDNP, g | 150.0 |
| Sly-Off 4000 Pt catalyst soln, g (25 drops) | 0.240 |
| Stabilizer, g | 0.50 |
| Total Batch, g | 300.74 |

Example 4

Preparation of Silicone Elastomer Gels

Anhydrous silicone elastomer gels having moderate polyether content (25 to 35% by weight) were prepared using Polycerin DUS-80, a α,ω-diallyl polypropylene oxide (PO) polyether having 20 PO units per molecule. Shown in Table 4 are three silicone elastomer gels made in D5 fluid, isododecane (IDD) and isodecyl neopentanoate (IDNP) carrier fluids, respectively. These gels contain 26 wt. % of polyether component in the gel network.

Gels were prepared by following these steps: 1) charge the all the components except catalyst to a glass container (or a reactor) and stir to homogeneous; 2) catalyze the reaction mixture and place the mixture in a 70° C. water bath and continue the stirring until the mixture gelled, 3) leave the reaction mixture container in the 70° C. water bath for a total of 4 hrs.

The total of components (A) and (B) constitutes the gel network, and is referred to as the initial elastomer content (IEC) in the gels in this invention. The type and the amount of carrier fluid, component (D), in these gels are shown below. The total of components (A), (B), and (D) sum to 100 parts. Platinum catalyst in component (C) was used at 3 to 5 ppm, based on the total of (A), (B), and (D). These gels were made to 20% initial elastomer content (IEC).

TABLE 4

Silicone elastomer gels based on PO20 polyether

| | Example # | | |
|---|---|---|---|
| | 4A | 4B | 4C |
| Component (A) | Example 1A | Example 1C | Example 1B |
| Component (B) | Polycerin DUS-80 (PO20 type) | Polycerin DUS-80 (PO20 type) | Polycerin DUS-80 (PO20 type) |
| SiH:Vi ratio | 1.00 | 1.00 | 1.00 |
| % IEC in gel | 20.0 | 20.0 | 20.0 |
| Wt. % Organics in gel | 26.4 | 26.4 | 26.4 |
| Carrier fluid type | D5 | IDD | IDNP |
| Actual amount | | | |
| Example 1A (50% solids in 245 fluid), g | 23.57 | | |
| Example 1C (50% solids in IDD), g | No | 23.57 | |
| Example 1B (50% solids in IDNP), g | No | | 23.56 |
| Polycerin DUS-80 extender, g | 4.24 | 4.26 | 4.25 |
| D5 fluid, g | 52.235 | | |
| Isododecane, g | | 52.22 | |
| IDNP, g | | | 52.26 |
| Syl-Off 4000, g | 0.06 | 0.06 | 0.06 |
| Total Batch, g | 80.11 | 80.11 | 80.13 |
| Gel appearance | Clear, slightly yellow | Clear, slightly yellow | Clear, slightly yellow |
| Texture analyzer, force 1, g | 387.0 | 220.1 | 90.0 |
| Texture analyzer, force-time 1-2, g | 2036.0 | 1177.3 | 484.2 |
| Gel hardness (as compression strength), N/m$^2$ | 29,954 | 17,036 | 6,966 |
| Viscosity of gel, N · s/m$^2$ or poise (dyne · s/cm$^2$) | 157,590 | 91,125 | 37,478 |

Example 5

Preparation of Silicone Elastomer Gels with Higher PO Content

Silicone elastomer gels of higher organic content were prepared by selecting the amount of components (A) and (B) (as used in Example 4) to give a lower [SiH]/[Vinyl] ratio in the composition. For instance, a [SiH]/[Vinyl] ratio of 0.80 was used to make the silicone elastomer gels in Table 5 which had 31% by weight of polyether in the gel network.

TABLE 5

Composition and property of silicone elastomer gels from PO20 polyether

| | Example # | | |
|---|---|---|---|
| | 5A | 5B | 5C |
| Component (A) | 1A | 1C | 1B |
| Component (B) | Polycerin DUS-80 (PO20 type) | Polycerin DUS-80 (PO20 type) | Polycerin DUS-80 (PO20 type) |
| [SiH]:[Vi] ratio | 0.80 | 0.80 | 0.80 |
| % IEC in gel | 20.0 | 20.0 | 20.0 |
| Wt. % Organics in gel | 31.0 | 31.0 | 31.0 |
| Carrier fluid type | 245 | IDD | IDNP |
| Actual amount | | | |
| Example 1A (50% solids in D5 fluid), g | 22.10 | | |
| Example 1C (50% solids in IDD), g | No | 22.10 | |
| Example 1B (50% solids in IDNP), g | No | | 22.11 |
| Polycerin DUS-80 PO20 extender, g | 4.96 | 4.95 | 4.96 |
| D5 fluid, g | 52.974 | | |
| Isododecane, g | | 52.955 | |
| IDNP (Ceraphyl SLK), g | | | 52.986 |
| Syl-Off 4000, g | 0.06 | 0.06 | 0.06 |
| Total Batch, g | 80.09 | 80.07 | 80.12 |
| Gel appearance | Clear, slightly yellow | Clear, slightly yellow | Clear, slightly yellow |
| Texture analyzer, force 1, g | 253.1 | 142.4 | 82.5 |
| Texture analyzer, force-time 1-2, g | 1342.0 | 767.4 | 446.3 |
| Gel hardness (as compression strength), $N/m^2$ | 19,590 | 11,022 | 6,386 |
| Viscosity of gel, $N \cdot s/m^2$ or poise ($dyne \cdot s/cm^2$) | 103,873 | 59,398 | 34,544 |

Example 6

Preparation of Silicone Elastomer Gels

Silicone elastomer gels were prepared from various organohydrogen siloxanes having a [SiH]/[Vinyl] ratio of 0.90 in different carrier fluids. The gel compositions, as summarized in Table 6, contained 28.5% by weight of polyether as derived from Polycerin DUS-80, and 47.9% by weight of polyether as derived from Unisafe PKA-5018 polyether. These gels were made using the procedure described above.

TABLE 6

Composition and properties of silicone elastomer gels from PO polyether

| | Example # | | | |
|---|---|---|---|---|
| | 6A | 6B | 6C | 6D |
| Component (A) | 1A | 1C | 1B | 1B |
| Component (B) | Polycerin DUS-80 (PO20 type) | Polycerin DUS-80 (PO20 type) | Polycerin DUS-80 (PO20 type) | PKA-5018 (PO50 type) |
| [SiH]:[Vi] ratio | 0.90 | 0.90 | 0.90 | 0.90 |
| % IEC in gel | 20.0 | 20.0 | 20.0 | 20.0 |
| Wt. % Organics in gel | 28.5 | 28.5 | 28.5 | 47.9 |
| Carrier fluid type | 245 | IDD | IDNP | IDNP |
| Actual amount | | | | |
| Example 1A (50% solids in 245), g | 85.81 | | | |
| Example 1C (50% solids in IDD), g | No | 85.80 | | |
| Example 1B (50% solids in IDNP), g | No | | 85.80 | 62.58 |
| Polycerin DUS-80 PO20 extender, g | 17.11 | 17.12 | 17.11 | |
| PKA-5018 PO50 extender, g | No | | | 28.73 |
| D5 fluid, g | 197.11 | | | |
| Isododecane, g | | 197.11 | | |
| Isodecyl Neopentanoate, g | | | 197.12 | 208.97 |
| Syl-Off 4000, g | 0.24 | 0.24 | 0.24 | 0.24 |
| Total Batch, g | 300.27 | 300.27 | 300.27 | 300.52 |
| Gel appearance | Clear, slightly yellow | Clear, slightly yellow | Clear, slightly yellow | Clear, slightly yellow |
| Texture analyzer, force 1, g | 271.7 | 177.7 | 94.7 | 178.4 |
| Texture analyzer, force-time 1-2, g | 1497.2 | 964.7 | 528.0 | 981.7 |
| Gel hardness (as compression strength), $N/m^2$ | 21,030 | 13,754 | 7,330 | 13,808 |
| Viscosity of gel, $N \cdot s/m^2$ or poise ($dyne \cdot s/cm^2$) | 115,886 | 74,670 | 40,868 | 75,985 |

Example 7

Preparation of Silicone Elastomer Gels with Low Elastomer Contents in Carrier Fluids Gels were formed in carrier fluids at very low initial elastomer content (IEC), as illustrated in Table 7. Gels in D5 fluid were obtained at 5.0% IEC by weight, i.e. total of components (A) and (B). Gels were also formed in IDD at 6.2% IEC by weight, as shown. The organic content of these gels were 28.5% in the ones derived from the PO20 ether and about 47.8% in the ones from PO50 polyether. A [SiH]/[Vinyl] ratio of 0.90 was used to make these silicone elastomer gels. These gels were made using the procedure described above.

TABLE 7

Composition and property of silicone elastomer gels of low elastomer contents

| | 7A | 7B | 7C | 7D |
|---|---|---|---|---|
| Component (A) | 1A | 1C | 1A | 1C |
| Component (B) | Polycerin DUS-80 (PO20 type) | Polycerin DUS-80 (PO20 type) | PKA-5018 (PO50 type) | PKA-5018 (PO50 type) |
| [SiH]:[Vi] ratio | 0.90 | 0.90 | 0.90 | 0.90 |
| Wt. % IEC in gel | 5.0 | 6.2 | 5.0 | 6.2 |
| Wt. % Organics in gel | 28.5 | 28.5 | 47.85 | 47.85 |
| Carrier fluid type | D5 | IDD | D5 | IDD |
| Formulation amount | | | | |
| Example 1A (50% solids in 245), g | 5.74 | | 4.20 | |
| Example 1C (50% solids in IDD), g | | 5.70 | | 4.21 |
| Polycerin DUS-80 PO20 extender, g | 1.17 | 1.26 | | |
| PKA-5018 PO50 extender, g | | | 1.94 | 1.93 |
| 245 fluid, g (d = 0.936 g/ml) | 73.17 | | 73.23 | |
| Isododecane, g (d = 0.74 g/ml) | | 57.188 | | 58 |
| Syl-Off 4000, g | 0.08 | 0.08 | 0.08 | 0.08 |
| Total Batch, g | 80.16 | 64.22 | 79.45 | 64.22 |
| Gel appearance | Clear, soft gel | Clear, very soft gel | Clear, soft gel | Clear, very soft gel |
| Texture analyzer, force 1, g | 4.81 | 2.78 | 6.95 | 8.22 |
| Texture analyzer, force-time 1-2, g | 34.35 | 22.20 | 47.55 | 54.08 |
| Gel hardness (as compression strength), N/m$^2$ | 372 | 215 | 538 | 636 |
| Viscosity of gel, N·s/m$^2$ or poise (dyne·s/cm$^2$) | 2,659 | 1,718 | 3,680 | 4,186 |

Example 8

Preparation of Silicone Elastomer Gels of High Elastomer Content and from Silicone and Polyether Mixture Extenders Anhydrous silicone elastomer gels of high elastomer content (35 to 50% by weight) were prepared using PICA-5018, a α,ω-diallyl poly(propylene oxide) (PO) polyether having 50 PO units per molecule. Variations of silicone elastomer gels may also be prepared by selecting the type and the amount of aliphatic unsaturated compound in the component (B) of this invention. For instance, a mixture of VINYL SILOXANE #2 and PKA-5018 α,ω-diallyl poly(propyleneoxide) (PO) polyether was used to prepare the gels shown in the Table 8 prepared in isododecane (IDD) and isodecyl neopentanoate (IDNP) carrier fluids. These gels contained 33 to 45 wt. % of polyether component in the gel network.

TABLE 8

Silicone elastomer gels from PO50 polyether and mixture of silicone/PO50 extenders

| | Example # | | |
|---|---|---|---|
| | 8A | 8B | 8C |
| Batch comments | 20% IEC Si-PO gel in IDNP/IDD solvents | 20% IEC Si-PO Hybrid gel in IDD/IDNP solvents | 20% IEC Si-PO Hybrid gel in IDD/IDNP solvents |
| Component (A): Example # | 1C | 1B | 1C |
| Component (B): Vinyl extender type | PKA-5018 (PO50 type) | PKA-5018 PO50 & 2-7891LV @ 70/30 | PKA-5018 PO50 & 2-7891LV @ 70/30 |
| [SiH]:[Vi] ratio | 1.00 | 1.00 | 1.00 |
| % IEC in gel | 20.0 | 20.0 | 20.0 |
| Wt. % Organics in gel | 45.2 | 33.6 | 33.6 |
| Carrier fluid type | IDNP/IDD | IDD/IDNP | IDNP/IDD |
| Wt % IDD in total solvents | 13.7 | 88.1 | 11.9 |
| Wt. % IDNP in solvents | 86.3 | 11.9 | 88.1 |
| Actual amount | | | |
| Example 1B (50% solids in IDNP), g | | 15.24 | |
| Example 1C (50% solids in IDD), g | 17.56 | | 15.27 |
| PKA-5018 PO50, g | 7.30 | 5.41 | 5.38 |
| Vinyl Siloxane #9, g | | 3.08 | 3.15 |
| Isododecane, g | | 56.4 | |
| IDNP (Ceraphyl SLK), g | 55.3 | | 56.6 |
| Syl-Off 4000, g | 0.08 | 0.08 | 0.08 |
| Total Batch, g | 80.24 | 80.21 | 80.48 |
| Gel appearance | Premix milky turned clear after IDNP add. Clear gel | Premix milky, turned clear after IDD add.. Clear gel | Premix milky, turned clear after IDNP add.. Clear gel |
| Texture analyzer, force 1, g | 327.3 | 160.8 | 321.2 |
| Texture analyzer, force-time 1-2, g | 1733.8 | 873.7 | 1705.9 |
| Gel hardness (as compression strength), N/m$^2$ | 25,334 | 12,446 | 24,861 |
| Viscosity of gel, N · s/m$^2$ or poise (dyne-s/cm$^2$) | 134,199 | 67,626 | 132,040 |

Example 9

Preparation of Silicone Elastomer Gels Based on Organohydrogensiloxanes and Mixture of Polyoxyalkylene and Vinyl Siloxane Silicone elastomer gels were prepared based organohydrogensiloxanes (component A) and mixture of polyoxypropylene and vinyl siloxane (component B), as summarized in Table 9. The procedures used were the same as described above.

TABLE 9

Silicone elastomer gels based organohydrogensiloxanes and mixture of polyoxypropylene and vinylsiloxane

| | Example # | |
|---|---|---|
| | 9A | 9B |
| Component A) | 1B | 1B |
| Component B) | PO50 | PO50 & VINYL-SILOXANE #2 @ 70/30 ratio. |
| Wt. % Organics in gel | 45.2 | 33.6 |
| SiH:Vi ratio | 1.00 | 1.00 |
| % IEC in gel | 20.0 | 20.0 |
| Carrier fluid | IDNP | IDNP |
| Actual formulation amount | | |
| Example 3 (50% solids in IDNP), g | 65.72 | 50.30 |
| PKA-5018 PO50, g | 27.16 | 14.83 |
| Vinyl Siloxane #9, g | | 20.03 |
| IDNP (Ceraphyl SLK), g | 207.14 | 214.89 |
| Syl-Off 4000, g (30 drops) | 0.24 | 0.24 |
| Total Batch, g | 300.26 | 300.29 |
| Gel appearance | Clear firm gel | Clear firm gel |

Example 10

Preparation of Silicone Elastomer Blends

Silicone elastomer blend in carrier fluids were prepared from silicone elastomer gels, according to this invention. To make silicone polyether elastomer blend, a silicone elastomer gel of known initial elastomer content (IEC) was prepared following the procedures detailed above. The silicone elastomer gels were then mechanically sheared or ground into small particle sizes, followed by further dilution with a carrier fluid to desired final elastomer content (FEC). The finished elastomer blend is an anhydrous dispersion of SPE gel particles of finite size swollen and suspended in carrier fluid. The SPE elastomer blend is clear and has a paste-like consistency.

Silicone polyether elastomer blends of this invention possess excellent thickening property in non-silicone type carrier fluids, particularly organic carrier fluids of polar types. To illustrate this benefit, silicone polyether elastomer blends in IDNP (isodecyl neopentanoate) were prepared using the SPE gels shown in the above examples.

Silicone polyether elastomer blends were made according to the following steps: 1) subject silicone elastomer gels from previous examples to mechanical shearing or grinding to reduce gels into finite particle size; 2) dilute with additional carrier fluid to desired final elastomer content (FEC); 3) incorporate an optional an vinyl fluid (VINYL SILOXANE #1), and subject the mixture to 70° C. for 2 hrs to effectively scavenging any residual SiH in the mixture. The wt % FEC is the total of components (A) and (B) in elastomer blend, where the total of components (A), (B), and (D) sum to 100 parts.

Two silicone polyether elastomer blends (SPE EB) in IDNP fluid were made according to the above method. Both elastomer blends have 10% elastomer gel content in IDNP: one from a SPE gel having 45.2% polyether content, the other from a SPE gel having 24.7% polyether content. The composition and property of these SPE EB's are found in Table 10.

TABLE 10

Silicone polyether elastomer blends in IDNP fluid

| | Example # | |
|---|---|---|
| | 10A | 10B |
| Gel sample Example # | 9A | 9B |
| Wt. % IEC in SPE gel | 20.0 | 20.0 |
| Wt. % Organics in gel | 45.2 | 24.7 |
| Carrier fluid type | IDNP | IDNP |
| SEB formulation amount | | |
| SPE gel used | 9A | 9B |
| SPE gel amount, g | 50.0 | 50.0 |
| Isodecyl Neopentanoate, g | 50.0 | 50.0 |
| VINYL SILOXANE #1, g | 0.20 | 0.20 |
| Total Batch, g | 100.20 | 100.20 |
| Appearance of SPE EB | Clear slightly yellow paste | Clear slightly yellow paste |
| Viscosity of SPE EB, cps | 584,000 | 349,056 |
| D(v0.5), μm | 6.49 | 15.91 |
| D(v0.9), μm | 24.3 | 33.89 |

The two SPE EB's in Table 9 are clear with paste-like consistency. The viscosities of these two elastomer blends are very high, indicative of excellent gelling effect in IDNP solvent.

Example 11

Preparation of Silicone Polyether Elastomer Blends in Organic Ester Carrier Fluid Silicone polyether elastomer blends (SEB) in either isododecane (IDD) or mixture of IDD and IDNP (isodecyl neopentanoate) were prepared as summarized in Table 11. All the SEB's here were made to about 10% FEC, and the relative amounts of IDD and IDNP in the component (D) tabulated. These elastomer blends have a clear appearance with a paste-like consistency.

TABLE 11

Silicone polyether elastomer blends in organic carrier fluids

| | Example # | | |
|---|---|---|---|
| | 11A | 11B | 11C |
| Gel Example # | 8A | 8B | 8C |
| Wt. % IEC in SPE gel | 20.0 | 20.0 | 20.0 |
| Wt. % Organics in gel | 45.2 | 33.6 | 33.6 |
| Carrier fluid type | IDNP/IDD | IDD/IDNP | IDNP/IDD |
| Wt % IDD in solvents | 6.1 | 94.7 | 5.3 |
| Wt. % IDNP in solvents | 93.9 | 5.3 | 94.7 |
| SEB formulation amount | | | |
| SPE gel used | 8A | 8B | 8C |
| SPE gel amount, g | 50.0 | 50.0 | 50.0 |
| Isododecane, g | | 50.0 | |
| Isodecyl Neopentanoate, g | 50.0 | | 50.0 |
| VINYL SILOXANE #1, g | 0.20 | 0.20 | 0.20 |
| Total Batch, g | 100.20 | 100.20 | 100.20 |
| Appearance of SEB | Clear paste | Clear paste | Clear paste |
| SEB Viscosity, cps | 191,063 | 150,625 | 185,188 |
| D(v0.5), μm | 20.3 | 38.1 | 18.5 |
| D(v0.9), μm | 39.1 | 54.1 | 42.0 |

Example 12

Preparation of Silicone Polyether Elastomer Blends

Silicone polyether elastomer blend of moderate polyether content were also prepared, following the method described above. Illustrated in Table 12 are three SPE EB's made from SPE gels having 28 wt. % polyether content and were made to 10% FEC in three different carrier fluids: DC245 silicone fluid, isododecane hydrocarbon solvent, and IDNP organic ester solvent.

TABLE 12

Silicone polyether elastomer blends in various carrier fluids

| | Example # | | |
|---|---|---|---|
| | 12A | 12B | 12C |
| Example # used | 6A | 6B | 6C |
| Wt % IEC in SPE gel | 20.0 | 20.0 | 20.0 |
| Wt. % Organics in gel | 28.5 | 28.5 | 28.5 |
| Carrier fluid type | D5 | IDD | IDNP |
| SEB formulation | | | |
| SPE gel used | 6A | 6B | 6C |
| SPE gel amount, g | 49.6 | 49.6 | 49.9 |
| D5 fluid, g | 49.6 | | |
| Isododecane, g | | 49.7 | |
| Isodecyl Neopentanoate, g | | | 49.9 |
| VINYL SILOXANE #1, g | 0.20 | 0.20 | 0.20 |
| Total Batch, g | 99.40 | 99.50 | 100.0 |
| Viscosity of SEB, cps | 44,231 | 39,929 | 268,611 |
| D(v, 0.5), μm | 29.9 | 40.3 | 210.2 |
| D(v, 0.9), μm | 45.2 | 57.2 | 333.5 |

Example 13

Preparation of Silicone Polyether Elastomer Blends

Silicone polyether elastomer blends having lower organic contents (lower than Example 12) as summarized in Table 13. These SPE EB's were prepared from SPE gels having 20% IEC.

TABLE 13

Silicone polyether elastomer blends in various carrier fluids.

| | Example # | | |
|---|---|---|---|
| | 13A | 13B | 13C |
| Gel Example # used | 4A | 4B | 4C |
| Wt. % IEC in SPE gel | 20.0 | 20.0 | 20.0 |
| Wt. % Organics in gel | 26.4 | 26.4 | 26.4 |
| Carrier fluid type | D5 | IDD | IDNP |
| SEB formulation | | | |
| SPE gel used | 4A | 4B | 4C |
| SPE gel amount, g | 49.5 | 49.7 | 49.8 |
| D5 fluid, g | 49.5 | | |
| Isododecane, g | no | 49.7 | |
| Isodecyl Neopentanoate, g | no | | 49.8 |
| VINYL SILOXANE #1, g | 0.20 | 0.20 | 0.21 |
| Total Batch, g | 99.20 | 99.60 | 99.81 |
| Appearance of SEB | Hazy viscous | Clear viscous | Clear, slightly yellowish paste |
| Viscosity of SEB, cps | 45,387 | 41,440 | 198,556 |
| D(v0.5), μm | 38.5 | 42.8 | 5.3 |
| D(v0.9), μm | 49.0 | 67.9 | 27.4 |

Example 14

Preparation of Actives Containing Silicone Polyether Elastomer Blend by Post-Load Method Silicone polyether elastomer blends (or gel paste) containing personal care actives were prepared from silicone polyether gels of this invention. The SPE gels made from above were ground into gel particles of desired size mechanically using a high-shear device. Actives were then mixed in, either neat or in a form of solution in cosmetic fluid, to disperse homogeneously in the elastomer blend. For instance, the elastomer blend 3B was prepared from the Example 2A gel by post adding vitamin A palmitate (VAP). The resulting 3B gel contained 4.75% by weight of VAP with a 9.5% final elastomer content (FEC) in IDNP solvent. The VAP-containing elastomer blend was a clear, paste with a characteristic VAP yellow. The VAP-containing SPE EB had excellent clarity and thickening effects in INDP, as indicated by its viscosity of 198,000 cps.

An example of SPE elastomer blend with higher VAP loading was also included in the table. About 10% of VAP was incorporated into the 3C SPE elastomer blend. Good clarity and high viscosity properties were maintained in this sample, attributed to the high polyether content in the gel network. A VAP-free SPE elastomer blend was included in the table for comparison.

TABLE 14

Vitamin containing silicone polyether elastomer blends by post-load method

| | Example # | | |
|---|---|---|---|
| | 14A | 14B | 14C |
| Composition description | EB in IDNP @ 10% FEC. | EB in IDNP @ 9.5% FEC. VAP post-loaded | EB in IDNP @ 10% FEC. VAP post-loaded |
| SPE gel Example # | 9A | 9A | 9A |
| Component (A): SiH intermediate | 1B | 1B | 1B |
| Component (B): Vinyl extender type | PKA-5018 PO50 | PKA-5018 PO50 | PKA-5018 PO50 |
| Wt % IEC in SPE gel | 20.0 | 20.0 | 20.0 |
| Active loading, % | 0.0 | 4.75 VAP | 10.0 VAP |
| % Organics in gel | 45.2 | 45.2 | 45.2 |
| Carrier fluid type | IDNP | IDNP | IDNP |
| SEB formulation | | | |
| SPE gel used | 9A | 9A | 9A |
| SPE gel amount, g | 49.5 | 49.5 | 49.6 |
| Isodecyl neopentanoate, g | 49.6 | 49.6 | 39.5 |
| Vinyl Siloxane #1 quencher, g | 0.21 | 0.23 | 0.20 |
| VAP/BHT (@ 98.5/1.5), g | 0.0 | 5.09 | 10.3 |
| Total Batch, g | 99.31 | 104.42 | 99.63 |
| Appearance of SEB | Clear, slightly yellow paste | Clear, yellow paste | clear, yellow paste |
| Viscosity, cps | 584,000 | 197,833 | 409,389 |
| D(v0.5), μm | 6.49 | 6.62 | 185.5 |
| D(v0.5), μm | 24.3 | 195.43 | 462.1 |

Example 15

Preparation of Actives Containing Silicone Polyether Elastomer Blend by Post-Load Method SPE elastomer blends containing as much as 30 wt % of ethylhexyl methoxycinnamate (or OMC, octyl methoxycinnamate) were prepared using the post-load method. These elastomer gel blends compositions and properties are summarized in Table 4.

TABLE 4

Silicone polyether elastomer blend with sunscreen post-loaded

| | Example # | | |
|---|---|---|---|
| | 15A | 15B | 15C |
| Composition description | SPE EB in IDNP @ 10% FEC. Active post-loaded | SPE EB in IDNP @ 10% FEC. Active post-loaded | SPE EB in IDNP @ 10% FEC. Active post-loaded |
| SPE gel Example # | 9A | 9A | 9A |
| Component (A): SiH int. | 1B | 1B | 1B |
| Component (B): Vinyl extender type | PKA-5018 PO50 | PKA-5018 PO50 | PKA-5018 PO50 |
| Wt % IEC in SPE | 20.0 | 20.0 | 20.0 |
| Active loading, wt. % | 10.0 OMC | 20.0 OMC | 30.0 OMC |

TABLE 4-continued

Silicone polyether elastomer blend with sunscreen post-loaded

| | Example # | | |
|---|---|---|---|
| | 15A | 15B | 15C |
| Wt. % Organics in gel | 45.2 | 45.2 | 45.2 |
| Carrier fluid type | IDNP | IDNP | IDNP |
| SEB formulation | | | |
| SPE gel used | 2A | 2A | 2A |
| SPE gel amount, g | 49.7 | 49.7 | 49.6 |
| Isodecyl neopentanoate, g | 39.9 | 29.8 | 19.8 |
| Vinyl Siloxane #1 quencher, g | 0.21 | 0.20 | 0.20 |
| OMC sunscreen, g; | 10.0 | 20.0 | 30.0 |
| Total Batch, g | 99.80 | 99.75 | 99.69 |
| Appearance of SEB | Clear, colorless paste | Clear, colorless paste | slightly cloudy, colorless paste |
| Viscosity, cps | 331,111 | 581,167 | 1,033,111 |
| D(v0.5), μm | 2.7 | 315.2 | 445.2 |
| D(v0.5), μm | 10.8 | 628.0 | 718.3 |

Example 16

Actives Post-Loaded Silicone Polyether Elastomer Blends from Gels of Mixed Silicone and Polyether Extenders The Example 2B gel was used to prepare a VAP-containing SPE elastomer blend following the post-load method. The finished SPE elastomer blend contained 4.75% by weight of VAP and was a clear yellowish paste having good thickening properties. A VAP-free SPE elastomer blend (Example #5A) was included in the following table for reference.

TABLE 5

Silicone polyether elastomer blends with Vitamin post-loaded

| | Example # | |
|---|---|---|
| | 16A | 16B |
| Composition description | SPE EB in IDNP @ 10% FEC. | SPE EB in IDNP @ 9.5% FEC. Active post-loaded |
| SPE gel ID | 9B | 9B |
| Component (A): SiH int. | 1B | 1B |
| Component (B): Vinyl extender type | PKA-5018 PO50 and Vinyl Siloxane #2 | PKA-5018 PO50 and Vinyl Siloxane #2 |
| Wt % IEC in SPE gel | 20.0 | 20.0 |
| Active loading, wt. % | 0.0 | 4.75 VAP |
| Wt. % Organics in gel | 24.7 | 24.7 |
| Carrier fluid type | IDNP | IDNP |
| SEB formulation amount | | |
| SPE gel used | 9B | 9B |
| SPE gel amount, g | 49.7 | 49.5 |
| Isodecyl neopentanoate, g | 49.7 | 49.6 |
| Vinyl Siloxane #1 quencher, g | 0.21 | 0.22 |
| VAP/BHT (@ 98.5/1.5), g | 0.0 | 5.08 |
| Total Batch, g | 99.61 | 104.40 |
| Appearance of SEB | Clear, slightly yellow paste | Clear, yellow paste |
| Viscosity, cps | 349,056 | 188,611 |
| D(v0.5), μm | 15.91 | 7.00 |
| D(v0.5), μm | 33.89 | 32.79 |

Example 17

Preparation of Active Pre-Loaded Silicone Polyether Gels

One unique property of silicone polyether gel is its excellent thickening property in non-silicone type cosmetic fluids, particularly organic cosmetic fluids of polar types. Another benefit of silicone polyether gel is its compatibility and miscibility with natural and organic actives. To illustrate this benefit, active containing silicone polyether gels in IDNP (isodecyl neopentanoate) were prepared.

Vitamin active was incorporated into silicone polyether gel using the pre-load method. The key advantage on using the preload method is that the active is entrapped within the cured gel network and potentially remained within the gel particles after processed into the elastomer blend products.

Two VAP-loaded silicone polyether gels ≳ 10% and 20% by weight respectively, were prepared as summarized in Table 17. VAP was uniformly dispersed throughout the gel samples, as judged by the appearance of the SPE gels.

These active-containing gels were prepared according to the following method:

1. The organohydrogensiloxane solution, diallyl polyether, and the cosmetic fluid of choice were mixed to homogeneous;
2. Vitamin A palmitate or active of choice was charged to the above mixture and stirred to homogeneous;
3. A catalytic amount of Pt catalyst solution was added;
4. Place the catalyzed mixture in a 70° C. (or specified) water bath and continue the stirring until the mixture gelled
5. Keep the mixture in the 70° C. (or specified) water batch for a total of 4 hrs.

TABLE 17

Vitamin preloaded silicone polyether gels

| | Example # | |
|---|---|---|
| | 17A | 17B |
| Composition description | SPE gel in IDNP solvent; 10% active pre-loaded | SPE gel in IDNP solvent; 20% active pre-loaded |

TABLE 17-continued

Vitamin preloaded silicone polyether gels

| | Example # | |
|---|---|---|
| | 17A | 17B |
| Component (A): SiH int. | 1B | 1B |
| Component (B): Vinyl extender type | PKA-5018 PO50 | PKA-5018 PO50 |
| Wt % IEC in gel | 20.0 | 20.0 |
| Active loading in gel, wt. % | 10.0 VAP | 20.0 VAP |
| Wt. % Organics in gel | 45.2 | 45.2 |
| Cosmetic fluid type | IDNP | IDNP |
| Formulation amount | | |
| Example 1B SiH int. (50% solids in IDNP), g | 17.52 | 17.52 |
| PKA-5018 PO50 extender, g | 7.28 | 7.35 |
| VAP/BHT (98.5/1.5), g | 8.32 | 16.63 |
| Isodecyl neopentanoate, g | 47.216 | 39.162 |
| Syl-Off 4000, g | 0.06 | 0.06 |
| Total Batch, g | 80.39 | 80.72 |
| Gel appearance | Clear yellow gel | Clear yellow gel |
| Texture analyzer, force 1, g | 56.7 | 40.9 |
| Texture analyzer, force-time 1-2, g | 306.9 | 210.2 |
| Gel hardness (as compression strength), $N/m^2$ | 4,389 | 3,166 |
| Viscosity of gel, $N \cdot s/m^2$ | 23,755 | 16,270 |

Example 18

Actives Preloaded SPE Gels from PO/Silicone Mixed Extenders

Additional examples of VAP pre-loaded silicone polyether gels were prepared from SPE gels derived from the mixture of PKA-5018 polyether and Vinyl Siloxane #2 dimethylvinyl-ended PDMS extenders as component (B), as summarized in Table 7. While these SPE gels had a lower polyether content, the VAP-loaded SPE gels had good clarity and the VAP remained uniformly dispersed throughout the gel matrix.

TABLE 7

Vitamin preloaded silicone polyether gels from mixed polyether/silicone extenders

| | Example # | |
|---|---|---|
| | 18A | 18B |
| Composition description | 20% IEC SPE Hybrid gel in IDNP solvent | 20% IEC SPE Hybrid gel in IDNP solvent |
| Component (A): SiH int. | 1B | 1B |
| Component (B): Vinyl extender type | PKA-5018 PO50 & Vinyl Siloxane #2 @ 70/30 ratio | PKA-5018 PO50 & Vinyl Siloxane #2 @ 70/30 ratio |
| Wt % IEC in gel | 20.0 | 20.0 |
| Active loading, wt. % | 10.0 VAP | 20.0 VAP |
| Wt. % Organics in gel | 33.6 | 33.6 |
| Cosmetic fluid type | IDNP | IDNP |
| Formulation amount | | |
| Example 1B SiH int. (50% solids in IDNP), g | 13.42 | 13.43 |
| PKA-5018 PO50 extender, g | 3.96 | 3.98 |
| Vinyl Siloxane #2 VEB, g | 5.34 | 5.34 |
| VAP/BHT (98.5/1.5), g | 8.33 | 16.63 |
| Isodecyl neopentanoate, g | 54.117 | 41.178 |
| Syl-Off 4000, g | 0.06 | 0.06 |
| Total Batch, g | 85.24 | 80.61 |
| Gel appearance | Clear yellow gel | Clear yellow gel |
| Texture analyzer, force 1, g | 85.5 | 80.9 |
| Texture analyzer, force-time 1-2, g | 454.0 | 430.4 |
| Gel hardness (as compression strength), $N/m^2$ | 6,618 | 6,262 |
| Viscosity of gel, $N\text{-}s/m^2$ | 35,140 | 33,314 |

Example 19

OMC Sunscreen Preloaded Silicone Polyether Gels

OMC sunscreen active was incorporated into SPE gels using the pre-load method. Examples of OMC at 10%, 20%, and 30% by weight respectively in SPE gels were prepared as summarized in Table 8. The cured SPE gels were solid gels with good hardness values. The OMC containing gels were clear up to 20% level, and cloudy at the 30% by weight of loading. OMC was uniformly dispersed through out the gels in all cases.

TABLE 8

OMC preloaded silicone polyether gels

| | Example # | | |
|---|---|---|---|
| | 19A | 19B | 19C |
| Composition description | SPE gel in IDNP solvent; 10% active pre-loaded | SPE gel in IDNP solvent; 20% active pre-loaded | SPE gel in IDNP solvent; 30% active pre-loaded |
| Component (A): SiH int. | 1B | 1B | 1B |
| Component (B): vinyl extender type | PKA-5018 PO50 | PKA-5018 PO50 | PKA-5018 PO50 |
| Wt % IEC in SPE gel | 20.0 | 20.0 | 20.0 |
| Active loading, wt. % | 10.0 OMC | 20.0 OMC | 30.0 OMC |
| Wt. % organics in gel | 45.2 | 45.2 | 45.2 |
| Cosmetic fluid type | IDNP | IDNP | IDNP |
| Formulation amount | | | |
| Example 1B SiH int. (50% solids in IDNP), g | 17.53 | 17.52 | 17.52 |
| PKA-5018 PO50 extender, g | 7.26 | 7.24 | 7.24 |

TABLE 8-continued

OMC preloaded silicone polyether gels

| | Example # | | |
|---|---|---|---|
| | 19A | 19B | 19C |
| OMC sunscreen, g | 8.03 | 16.13 | 24.24 |
| Isodecyl neopentanoate, g | 47.229 | 39.632 | 31.734 |
| Syl-Off 4000, g | 0.06 | 0.06 | 0.06 |
| Total Batch, g | 80.11 | 80.58 | 80.79 |
| Gel appearance | Clear colorless gel | Clear gel | Cloudy white gel |
| Texture analyzer, force 1, g | 98.5 | 75.3 | 38.6 |
| Texture analyzer, force-time 1-2, g | 528.9 | 405.9 | 214.1 |
| Gel hardness N/m$^2$ | 7,624 | 5,828 | 2,988 |
| Viscosity of gel, N · s/m$^2$ | 40,938 | 31,417 | 16,572 |

Example 20

OMC Preloaded SPE Gels from PO/Silicone Mixed Extenders

Additional examples of incorporating OMC using the preload method are shown for SPE gels derived from the mixture of diallyl polyether and dimethylvinyl-ended PDMS silicone as component (B). OMC loading was 10, 20, and 30% by weight respectively in the following examples. These OMC-containing SPE gels also exhibit good hardness property and uniformity in appearance.

TABLE 20

OMC preloaded silicone polyether gels from mixed extenders

| | Example # | | |
|---|---|---|---|
| | 20A | 20B | 20C |
| Composition description | 20% IEC SPE hybrid gel in IDNP solvent | 20% IEC SPE hybrid gel in IDNP solvent | 20% IEC SPE hybrid gel in IDNP solvent |
| Component (A): SiH int. | 1B | 1B | 1B |
| Component (B): Vinyl extender type | PKA-5018 PO50 & Vinyl Siloxane #2 @ 70/30 ratio | PKA-5018 PO50 & Vinyl Siloxane #2 @ 70/30 ratio | PKA-5018 PO50 & Vinyl Siloxane #2 @ 70/30 ratio |
| SiH:Vi ratio | 1.00 | 1.00 | 1.00 |
| % IEC in gel | 20.0 | 20.0 | 20.0 |
| Active loading, wt. % | 10.0 OMC | 20.0 OMC | 30.0 OMC |
| Wt. % Organics in gel | 33.6 | 33.6 | 33.6 |
| Carrier fluid type | IDNP | IDNP | IDNP |
| Formulation amount | | | |
| Example # SiH int. (50% solids in IDNP), g | 13.42 | 13.43 | 13.43 |
| PKA-5018 PO50 extender, g | 3.96 | 3.97 | 3.99 |
| Vinyl Siloxane #2, g | 5.36 | 5.37 | 5.36 |
| OMC sunscreen, g | 8.04 | 16.14 | 24.24 |
| Isodecyl neopentanoate, g | 49.922 | 41.68 | 33.862 |
| Syl-Off 4000, g | | 0.06 | 0.06 |
| Total Batch, g | 80.70 | 80.64 | 80.94 |
| Gel appearance | Clear colorless gel | Clear colorless gel | Cloudy white gel |
| Texture analyzer, force 1, g | 128.5 | 107.3 | 18.1 |
| Texture analyzer, force-time 1-2, g | 691.2 | 577.7 | 103.9 |
| Gel hardness, N/m$^2$ | 9,946 | 8,305 | 1,401 |
| Viscosity of gel, N · s/m$^2$ | 53,500 | 44,715 | 8,042 |

Example 21

Preparation of Elastomer Blends from Actives Preloaded Gels:

Silicone polyether elastomer blends containing OMC sunscreen were prepared from OMC preloaded SPE gels made according to the current invention. Elastomer blends having 5%, 10% and 15% OMC in IDNP were made from OMC preloaded gels of high polyether content. The appearance, viscosity and gel particle size in these SPE elastomer blends are shown in the following table.

TABLE 10

OMC containing silicone polyether elastomer blend by pre-load method

| | Example # | | |
|---|---|---|---|
| | 21A | 21B | 21C |
| Composition description | SPE EB in IDNP @ 10% FEC; 5% OMC loaded. | SPE EB in IDNP @ 10% FEC; 10% OMC loaded. | SPE EB in IDNP @ 10% FEC; 15% OMC loaded. |
| SPE gel Example # | 19A | 19B | 19C |
| Component (A): SiH int. | 1B | 1B | 1B |
| Component (B): Vinyl extender type | PKA-5018 PO50 | PKA-5018 PO50 | PKA-5018 PO50 |
| Wt % IEC in SPE gel | 20.0 | 20.0 | 20.0 |
| % Active in starting gel | 10.0% OMC | 20.0% OMC | 30.0% OMC |
| Wt. % VAP in final SEB | 5.0% OMC | 10.0% OMC | 15.0% OMC |
| Wt. % organics in gel | 45.2 | 45.2 | 45.2 |
| Cosmetic fluid type | IDNP | IDNP | IDNP |
| SEB formulation | | | |
| gel used | 8A | 8B | 8C |
| organohydrogensiloxane amount, g | 49.8 | 49.7 | 49.6 |
| Isodecyl neopentanoate, g | 49.7 | 49.7 | 49.6 |
| Vinyl Siloxane #1 Quencher, g | 0.21 | 0.22 | 0.21 |
| Total Batch, g | 99.71 | 99.60 | 99.49 |
| Appearance of SEB | clear, colorless paste | clear, colorless paste | slightly hazy, colorless liquid |
| Viscosity, cps | 294,333 | 277,889 | 3,378 |
| D(v0.5), μm | 5.269 | 3.529 | 41.246 |
| D(v0.5), μm | 23.19 | 15.36 | 47.47 |

Example 22

SPE Elastomer Blends from VAP Preloaded Gels from PO/Silicone Mixed Extenders

Examples of VAP containing elastomer blends were made from VAP preloaded SPE gels derived from a mixture of PICA-5018 polyether and Vinyl Siloxane #2 dimethylvinyl-terminated PDMS as component (B) in the invention, as summarized Table 22. The SPE elastomer blends prepared from VAP preloaded gels were clear yellow pastes with excellent thickening property in IDNP cosmetic fluids.

TABLE 22

VAP loaded silicone polyether elastomer blend by pre-load method

| | Example # | |
|---|---|---|
| | 22A | 22B |
| Composition description | SPE EB in IDNP @ 10% FEC; VAP loaded. | SPE EB in IDNP @ 10% FEC; VAP loaded. |
| SPE gel Example # | 18A | 18B |
| Component (A): SiH int. | 1B | 1B |
| Component (B): Vinyl extender type | PKA-5018 PO50 & Vinyl Siloxane #2 | PKA-5018 PO50 & Vinyl Siloxane #2 |
| % IEC in starting gel | 20.0 | 20.0 |
| Wt. % active in starting gel | 10.0% VAP | 20.0% VAP |
| Wt. % VAP load in final SEB | 5.0% VAP | 10.0% VAP |
| Wt. % Organics in gel | 24.7 | 24.7 |
| Cosmetic fluid type | IDNP | IDNP |
| SEB formulation amount | | |
| Gel used | 7A | 7B |
| ORGANOHYDROGENSILOXANE gel amount, g | 49.5 | 50.0 |
| Isodecyl neopentanoate, g | 49.5 | 50.0 |
| Vinyl Siloxane #1 quencher, g | 0.20 | 0.20 |
| Total Batch, g | 99.20 | 100.20 |
| Appearance of SEB as made | Clear, yellowish paste | Clear, yellowish paste |
| Viscosity, cps | 177,556 | 160,222 |
| D(v0.5), μm | 9.533 | 23.813 |
| D(v0.5), μm | 29.56 | 45.72 |

The invention claimed is:

1. A gel composition comprising a silicone polyether elastomer from the reaction of:
   A) an organohydrogensiloxane prepared by a hydrosilylation reaction of;
      a) an organohydrogencyclosiloxane having the formula $[(CH_3)HSiO]_g$ where g is 3-8 and,
   B) a compound or mixture of compounds having at least two aliphatic unsaturated hydrocarbon groups in its molecule selected from a vinyl functional or hexenyl functional polydimethylsiloxane having the average formula, $CH_2=CH(Me)_2SiO[Me_2SiO]_xSi(Me)_2CH=CH_2$ $CH_2=CH-(CH_2)_4(Me)_2SiO[Me_2SiO]_xSi(Me)_2-(CH_2)_4-CH=CH_2$, or $Me_3SiO[(Me)_2SiO]_x[CH_2=CH(Me)SiO]_ySiMe_3$, wherein Me is methyl, $x \geq 0$ and $y \geq 2$, and wherein the molar ratio of SiH units to unsaturated group ranges from 2/1 to 8/1,
   $B^3$) a polyether compound or mixture of polyether compounds having the formula $R^2-Y-R^2$ where $R^2$ is a monovalent unsaturated aliphatic group and Y is a polyoxyalkylene group having the formula $-[(C_2H_4O)_c(C_3H_6O)_d(C_4H_8O)_e]-$ where c, d, and e may each independently range from 0 to 200, providing the sum of c+d+e is greater than 2
   C) a hydrosilylation catalyst, and
   D) a carrier fluid selected from decamethylcyclopentasiloxane, isododecane, or isodecyl neopentanoate,
   wherein the gel composition has a compression hardness of at least 200 Newton/m².

2. The composition of claim 1 further comprising
   E) a personal care or healthcare active.

3. The composition of claim 1 wherein $B^3$) the polyether compound is selected from the group $H_2C=CHCH_2[C_3H_6O]_dCH_2CH=CH_2$ $H_2C=CH[C_3H_6O]_dCH=CH_2$ $H_2C=C(CH_3)CH_2[C_3H_6O]_dCH_2C(CH_3)=CH_2$ $HC=CCH_2[C_3H_6O]_dCH_2C=CH$, and $HC=CC(CH_3)_2[C_3H_6O]_dC(CH_3)_2C=CH$ where d is greater than 2.

4. The composition of claim 1 wherein C) the hydrosilylation catalyst is a platinum group containing catalyst.

5. The composition of claim 2 wherein E) is a personal care active selected from a vitamin, sunscreen, plant extract, or fragrance.

6. The composition of claim 2 wherein E) is a health care active selected from a topical drug active, protein, enzyme, antifungal, or antimicrobial agent.

7. The composition of claim 2 wherein component E) is vitamin A palmitate.

8. The composition of claim 2 wherein component E) is octyl methoxycinnamate.

* * * * *